(12) United States Patent
Sano et al.

(10) Patent No.: US 8,758,253 B2
(45) Date of Patent: Jun. 24, 2014

(54) ULTRASONIC PROBE AND ULTRASONIC DIAGNOSTIC APPARATUS USING THE SAME

(75) Inventors: Shuzo Sano, Tokyo (JP); Akifumi Sako, Tokyo (JP); Takashi Kobayashi, Tokyo (JP); Mikio Izumi, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 595 days.

(21) Appl. No.: 12/513,858

(22) PCT Filed: Nov. 6, 2007

(86) PCT No.: PCT/JP2007/071516
§ 371 (c)(1),
(2), (4) Date: May 7, 2009

(87) PCT Pub. No.: WO2008/056643
PCT Pub. Date: May 15, 2008

(65) Prior Publication Data
US 2010/0036257 A1 Feb. 11, 2010

(30) Foreign Application Priority Data

Nov. 8, 2006 (JP) ................. 2006-302627

(51) Int. Cl.
*A61B 8/14* (2006.01)
*A61B 8/00* (2006.01)

(52) U.S. Cl.
CPC .................................... *A61B 8/4281* (2013.01)
USPC .............................. 600/459; 73/570; 310/322

(58) Field of Classification Search
USPC ............. 600/459; 367/153, 181, 188; 73/632, 73/633, 861.18, 861.23–861.26
See application file for complete search history.

(56) References Cited

U.S. PATENT DOCUMENTS 5,894,452 A 4/1999 Ladabaum et al.
5,997,481 A * 12/1999 Adams et al. ................. 600/459
(Continued)

FOREIGN PATENT DOCUMENTS

DE 10 2005 014 836 A1 10/2005
JP 06-205772 7/1994
(Continued)

OTHER PUBLICATIONS

Supplementary European Search Report, dated Nov. 16, 2010, issued in corresponding European Patent Application No. 07 83 1248.
(Continued)

*Primary Examiner* — Unsu Jung
*Assistant Examiner* — Daniel Huntley
(74) *Attorney, Agent, or Firm* — Antonelli, Terry, Stout & Kraus, LLP.

(57) ABSTRACT

An ultrasonic probe is disclosed which includes a cMUT chip having a plurality of vibration elements whose electromechanical coupling coefficient or sensitivity is changed according to a bias voltage and transmitting and receiving ultrasonic waves, an acoustic lens arranged above the cMUT chip, and a backing layer arranged below the cMUT chip. An electric leakage preventing unit is provided at the ultrasonic wave transmission/reception surface side of the acoustic lens or between the acoustic lens and the cMUT chip. The electric leakage preventing unit can be, for example, an insulating layer such as a ground layer. Such a structure makes it is possible to provide an ultrasonic probe capable of preventing electric leakage from the ultrasonic probe to an object to be examined so as to improve the electric safety and an ultrasonic diagnostic apparatus using the probe.

6 Claims, 15 Drawing Sheets

(56) References Cited

U.S. PATENT DOCUMENTS

Figure 1:
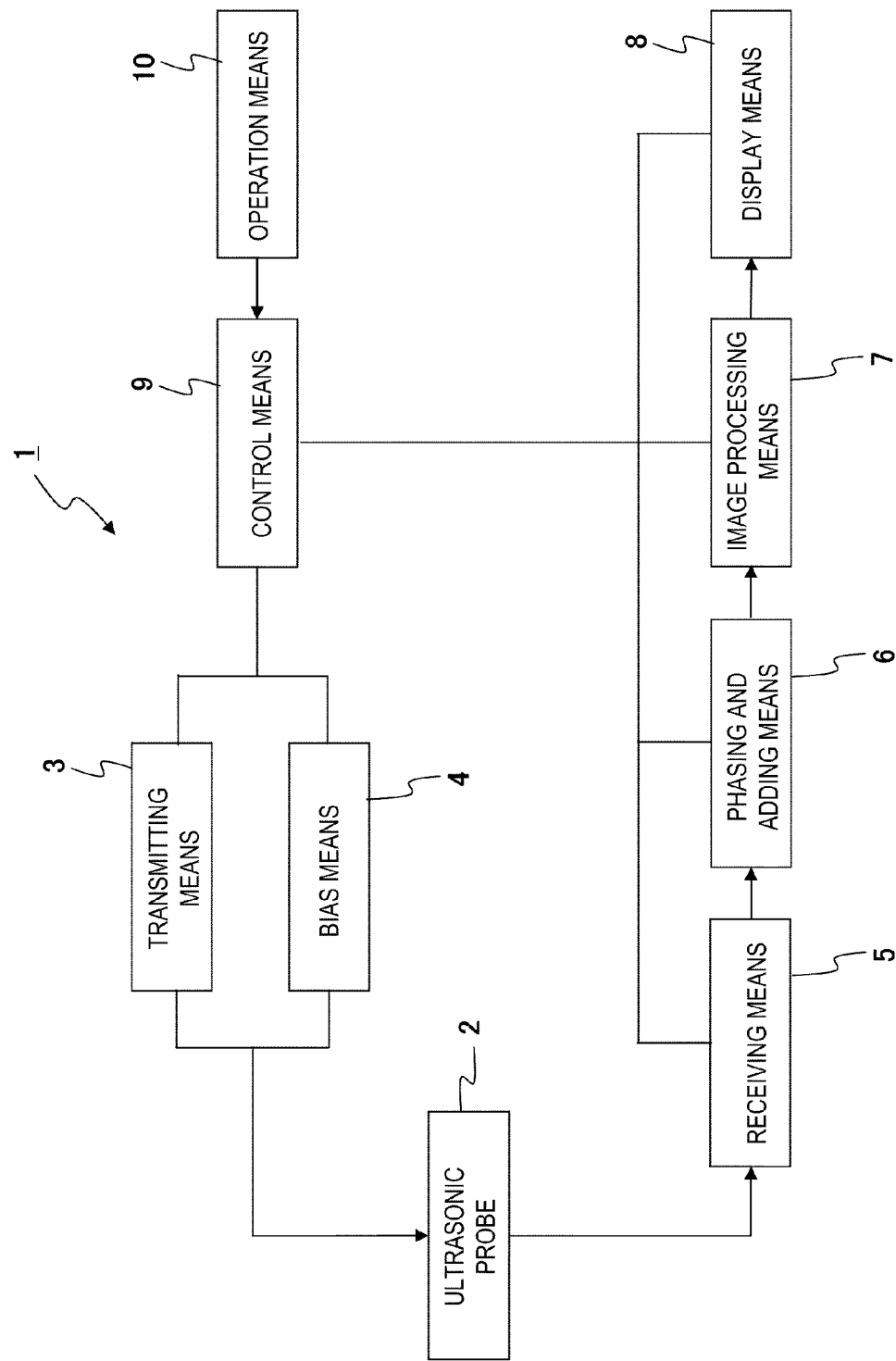

| | | | |
|---|---|---|---|
| 6,002,163 A * | 12/1999 | Wojnarowski | 257/620 |
| 6,592,525 B2 * | 7/2003 | Miller et al. | 600/459 |
| 2005/0075572 A1 | 4/2005 | Mills et al. | |
| 2005/0075573 A1 * | 4/2005 | Park et al. | 600/459 |
| 2006/0184033 A1 * | 8/2006 | Cerofolini | 600/459 |
| 2006/0184035 A1 | 8/2006 | Kimura et al. | |

FOREIGN PATENT DOCUMENTS

| | | |
|---|---|---|
| JP | 06-205772 A | 7/1994 |
| JP | 2006-166985 | 6/2006 |
| JP | 2006-166985 A | 6/2006 |
| JP | 2007-235795 | 9/2007 |
| WO | WO 2006/041058 A1 | 4/2006 |

OTHER PUBLICATIONS

State Intellectual Property Office of People's Republic of China, Application No. 200780041417.0, Hitachi Medical Corporation, Issuing Date: Apr. 24, 2012.

Communication pursuant to Article 94(3) EPC, Hitachi Medical Corporation, Application No. 07 831 248.5-1265, Dated Jun. 12, 2012.

\* cited by examiner

ULTRASONIC PROBE AND ULTRASONIC DIAGNOSTIC APPARATUS USING THE SAME

TECHNICAL FIELD

The present invention relates to an ultrasonic probe and ultrasonic diagnostic apparatus using the same, and more particularly to an ultrasonic probe and ultrasonic diagnostic apparatus using the same wherein the electric safety for an object to be examined is improved.

BACKGROUND ART

An ultrasonic diagnostic apparatus is for imaging diagnostic images based on the echo signals and the reflected signals thereof outputted from an ultrasonic probe. In an ultrasonic probe, a plurality of ultrasonic transducers is disposed. The ultrasonic transducers convert driving signals into ultrasonic waves and transmit them to the object, as well as receive the reflected echo signals produced from the object and convert them into electric signals.

In recent years, ultrasonic probes using a cMUT (Capacitive Micromachined Ultrasonic Transducer) have been developed. The cMUT is an ultrafine capacitance ultrasonic transducer manufactured by semiconductor microfabrication process as disclosed, for example, in Patent document 1. In the cMUT, bias voltage is applied on two electrodes (the object side and the backing layer side) disposed in a plurality of pairs opposite each other in a direction parallel to the ultrasonic wave transmitting/receiving surface, driving signals are superimposed and applied, and ultrasonic waves are sent out.

Patent Document 1: U.S. Pat. No. 5,894,452
Patent Document 2: JP-A-2007-235795

DISCLOSURE OF THE INVENTION

Problems to be Solved

However, the present inventors found out the problem described below as a result of reviewing the above-mentioned conventional technique.

That is, in the conventional ultrasonic probe using the conventional PZT, only one kind of driving signal is to be applied as voltage between the electrodes disposed opposite each other on the ultrasonic wave transmitting/receiving surface, whereby capable of reducing the current passing from the electrode toward the object by contacting the ground electrode to the electrode disposed on the object side as disclosed in, for example, Patent Document 2. However, in the ultrasonic probe using a cMUT, since the bias voltage is mainly applied to the electrode on the backing layer side at the same time as the driving signal formed by a high-frequency wave (drive voltage) is applied to the electrode on the object side, the ground layer cannot be contacted to the electrode on the object side directly, thus the insulation becomes insufficient unless a ground layer is provided.

Also, while there are cases in the ultrasonic probe using a cMUT that an acoustic matching layer is not provided, which causes the problem of deterioration in insulation construction.

The objective of the present invention is to provide an ultrasonic probe using a cMUT and an ultrasonic diagnostic apparatus using the same capable of preventing electrical leakage on the object by providing adequate insulation configuration in an ultrasonic probe using a cMUT, improved in electrical safety.

Means to Solve the Problem

In accordance with the present invention, the ultrasonic probe comprises:

a cMUT chip having a plurality of vibration elements wherein electromechanical coupling coefficient or sensitivity varies in accordance with bias voltage, for transmitting/receiving ultrasonic waves;

an acoustic lens provided on the upper part of the cMUT chip; and a backing layer provided on the lower part of the cMUT chip, characterized in further comprising electric leakage preventing means on the side of ultrasonic wave transmitting/receiving surface of the acoustic lens or between the acoustic lens and the cMUT chip.

Effect of the Invention

In accordance with the present invention, it is possible to provide an ultrasonic probe using a cMUT and an ultrasonic diagnostic apparatus using the same improved in electrical safety capable of preventing electric leakage to an object by providing adequate insulation configuration.

BRIEF DESCRIPTION OF THE DIAGRAMS

Figure 2:
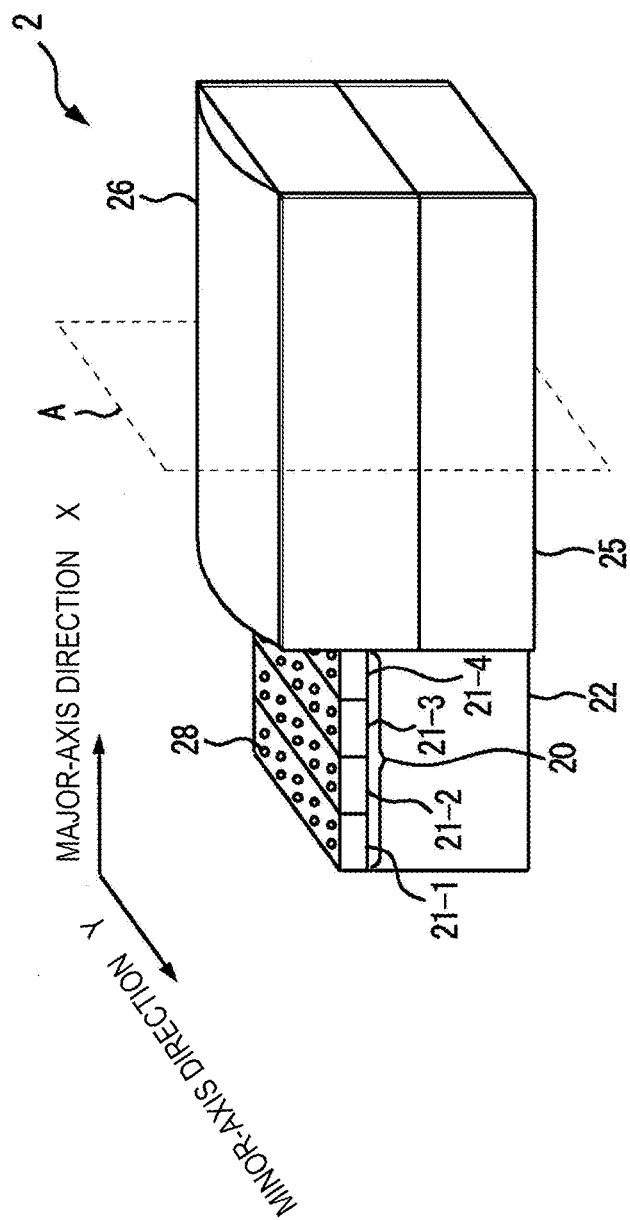
Figure 3:
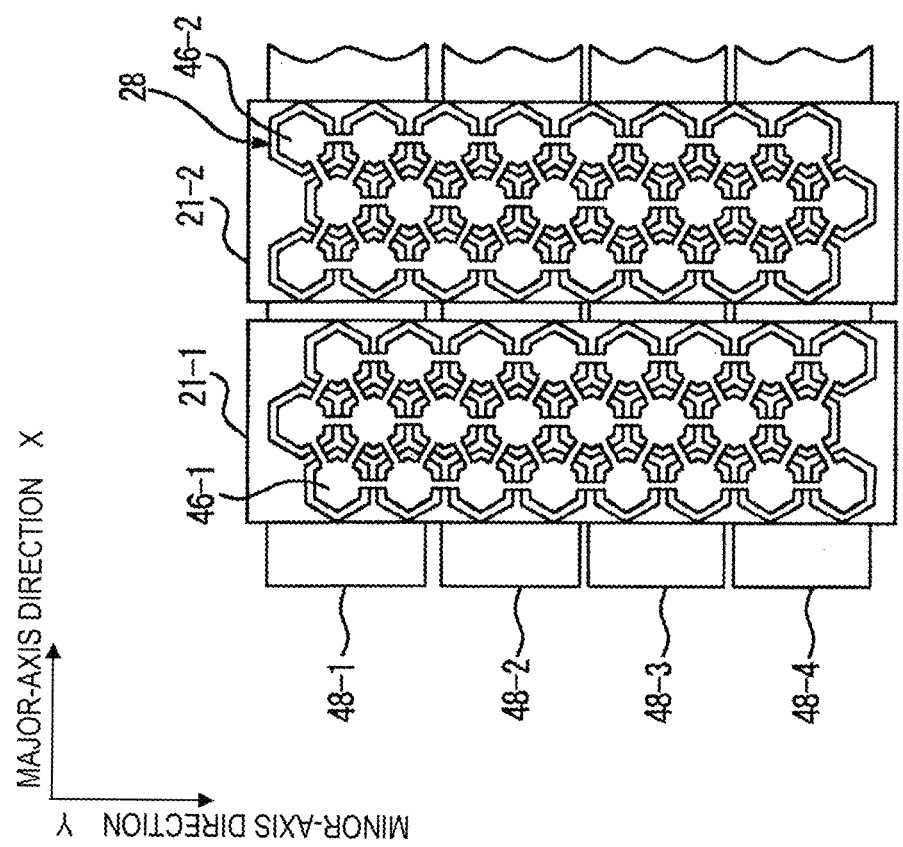
Figure 4:
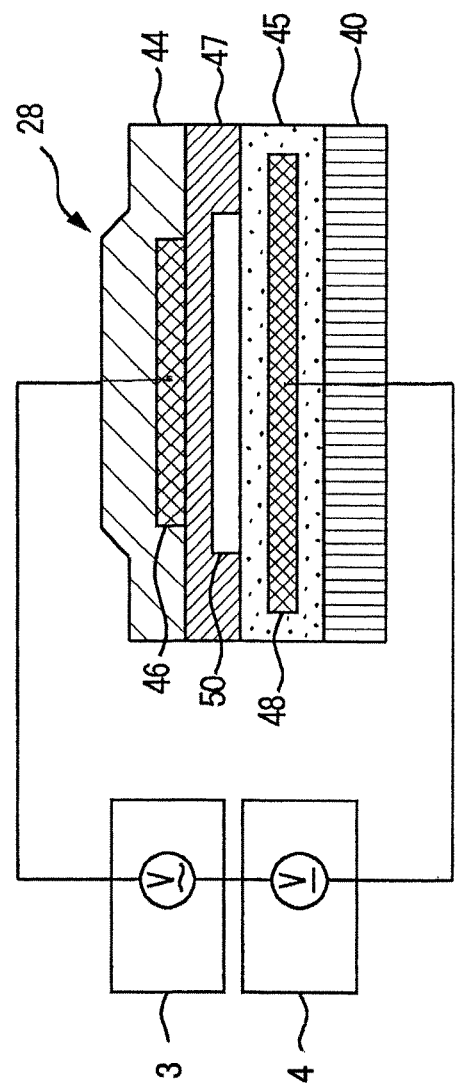
Figure 5:
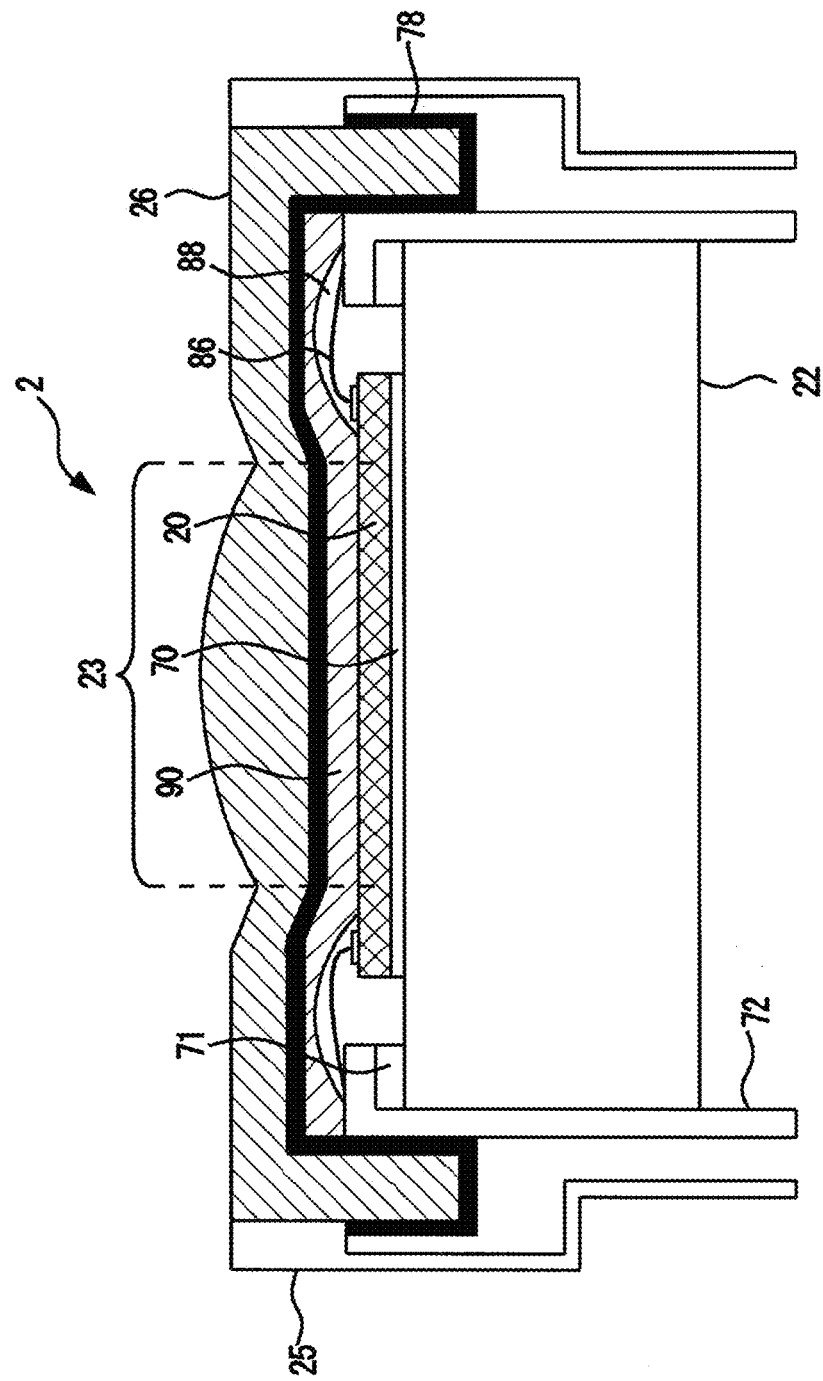
Figure 6:
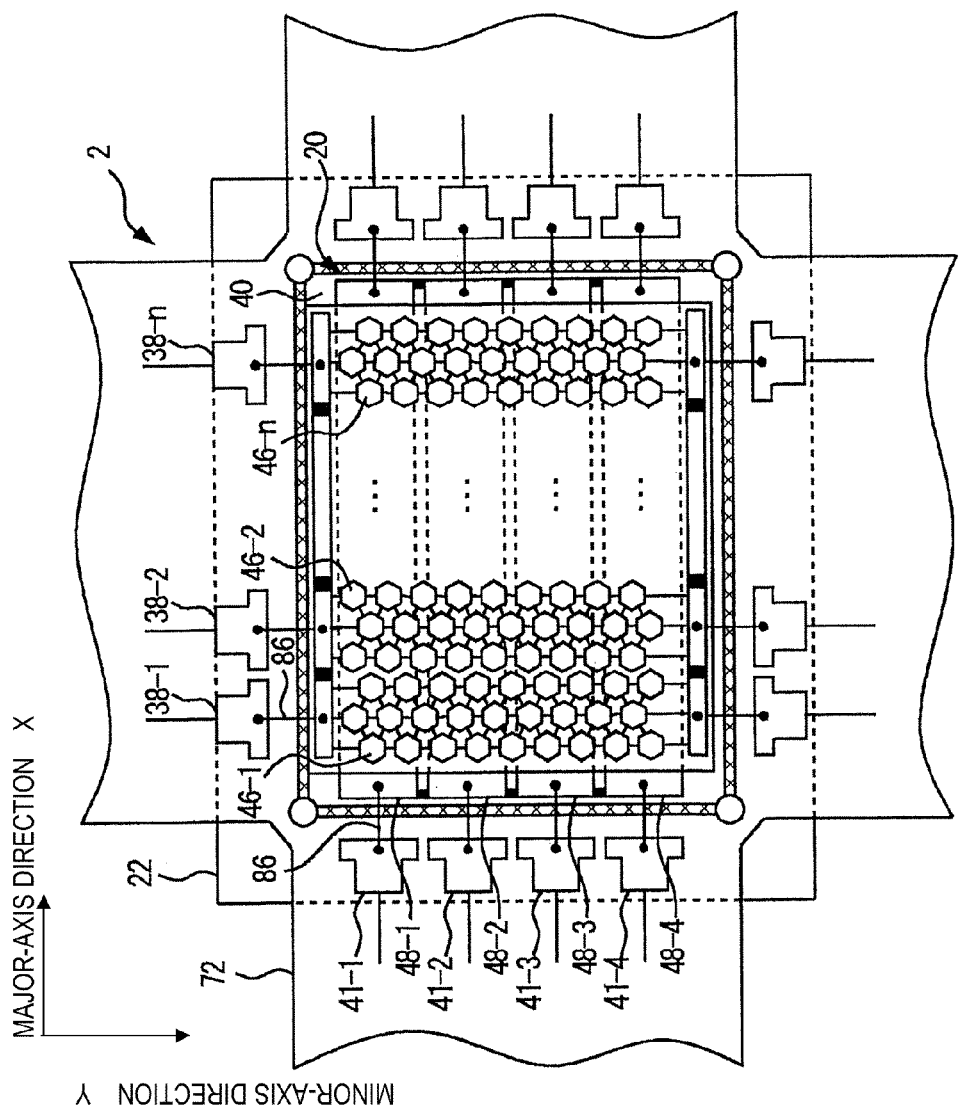
Figure 7:
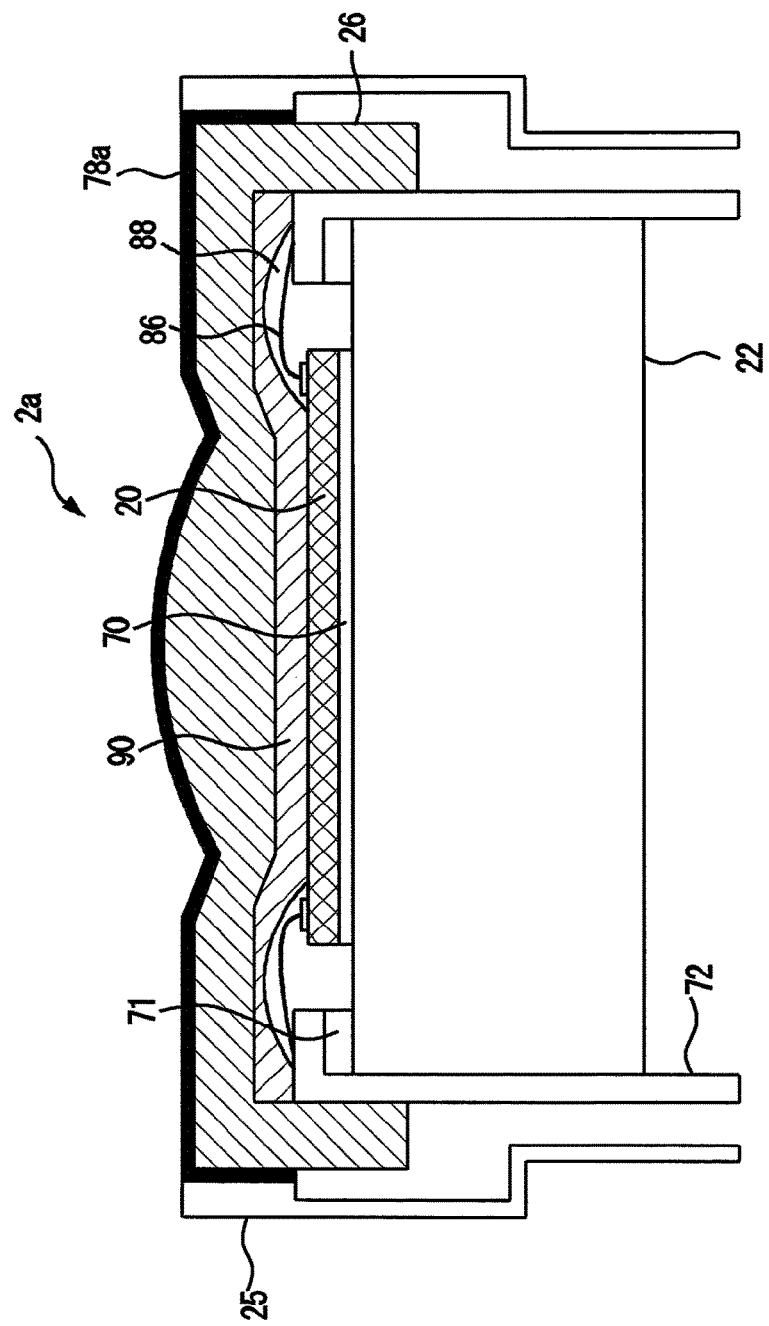
Figure 8:
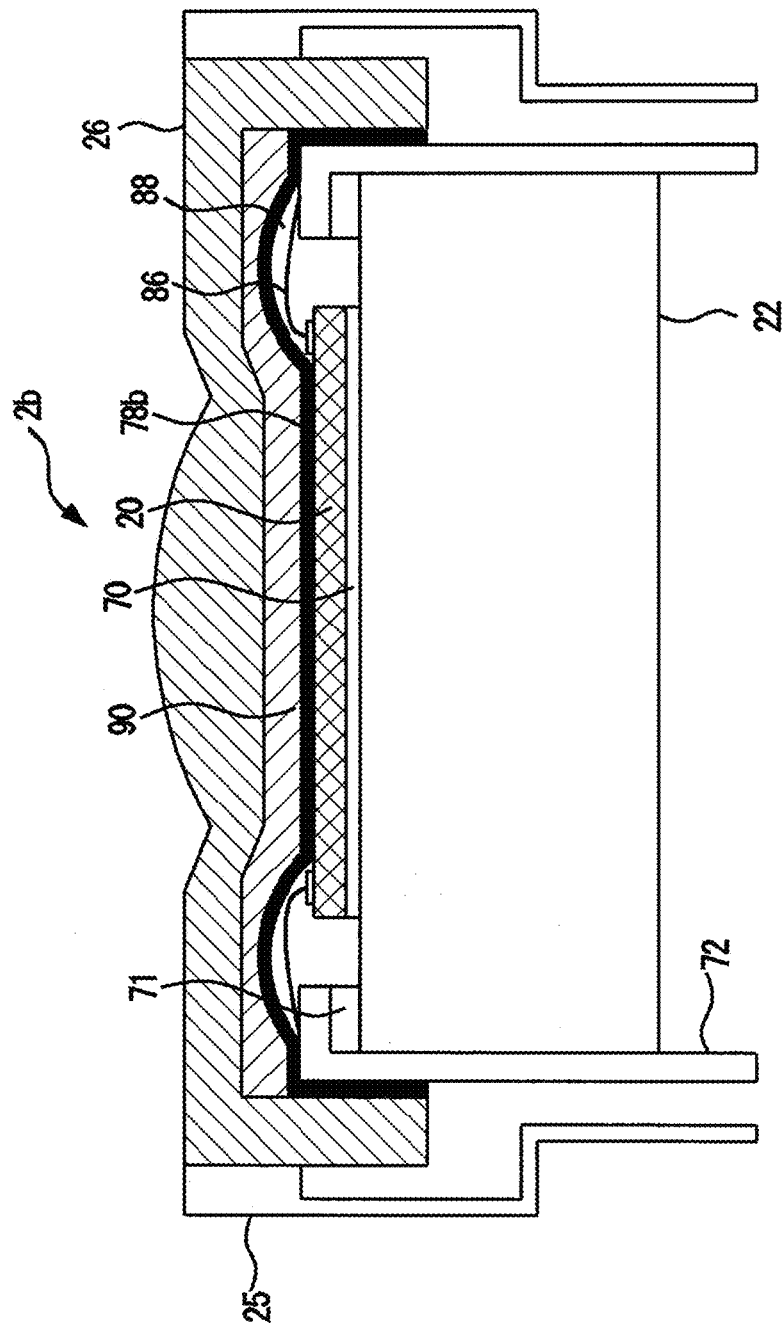
Figure 9:
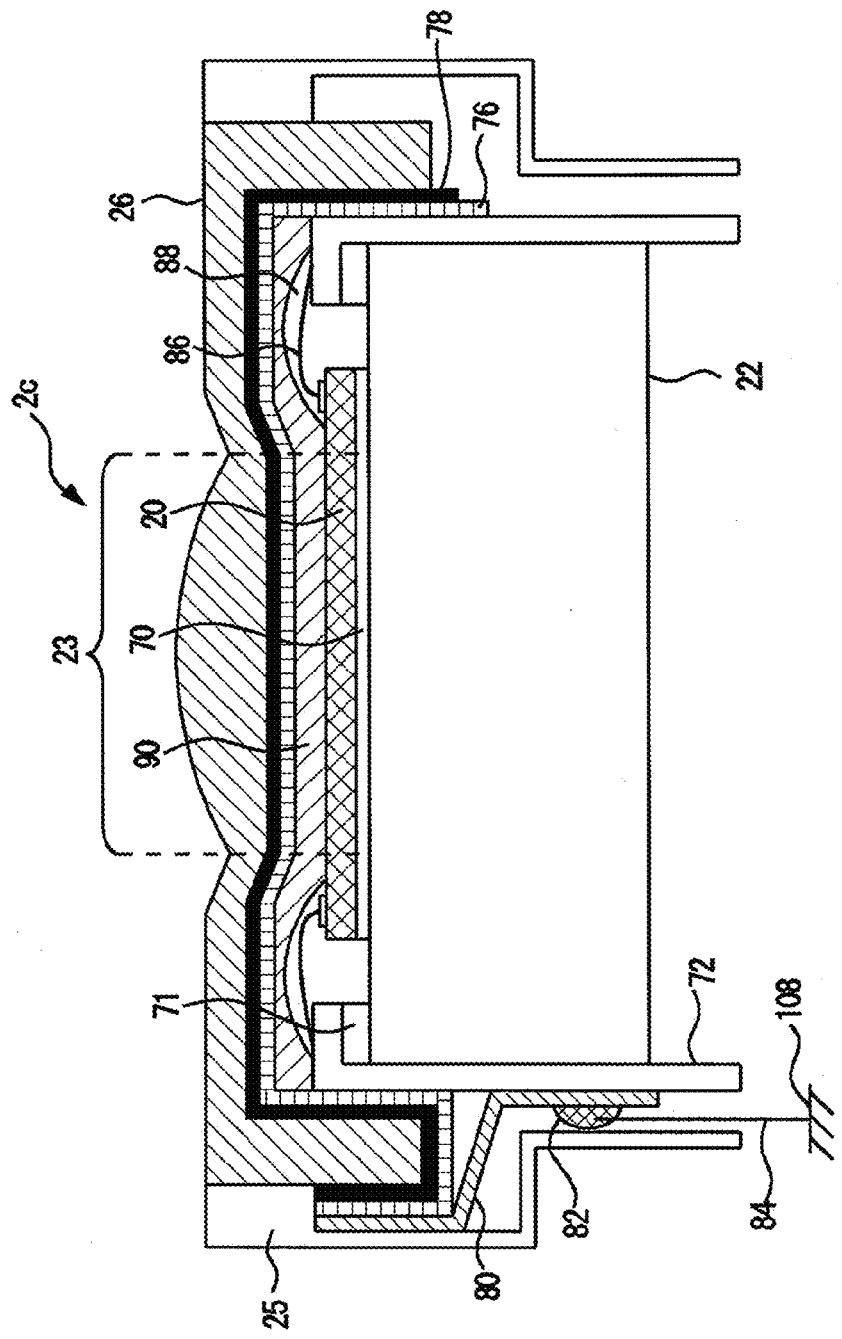
Figure 10:
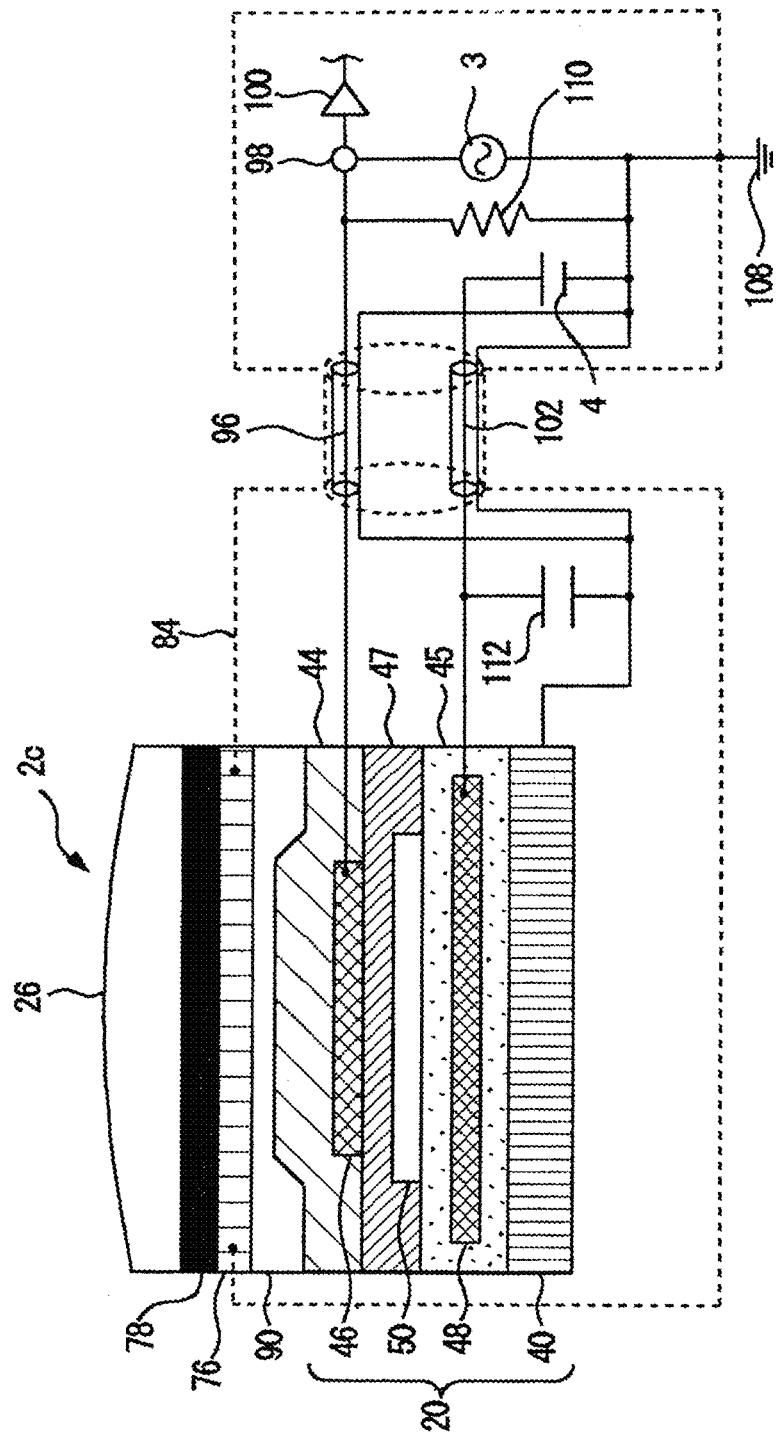
Figure 11:
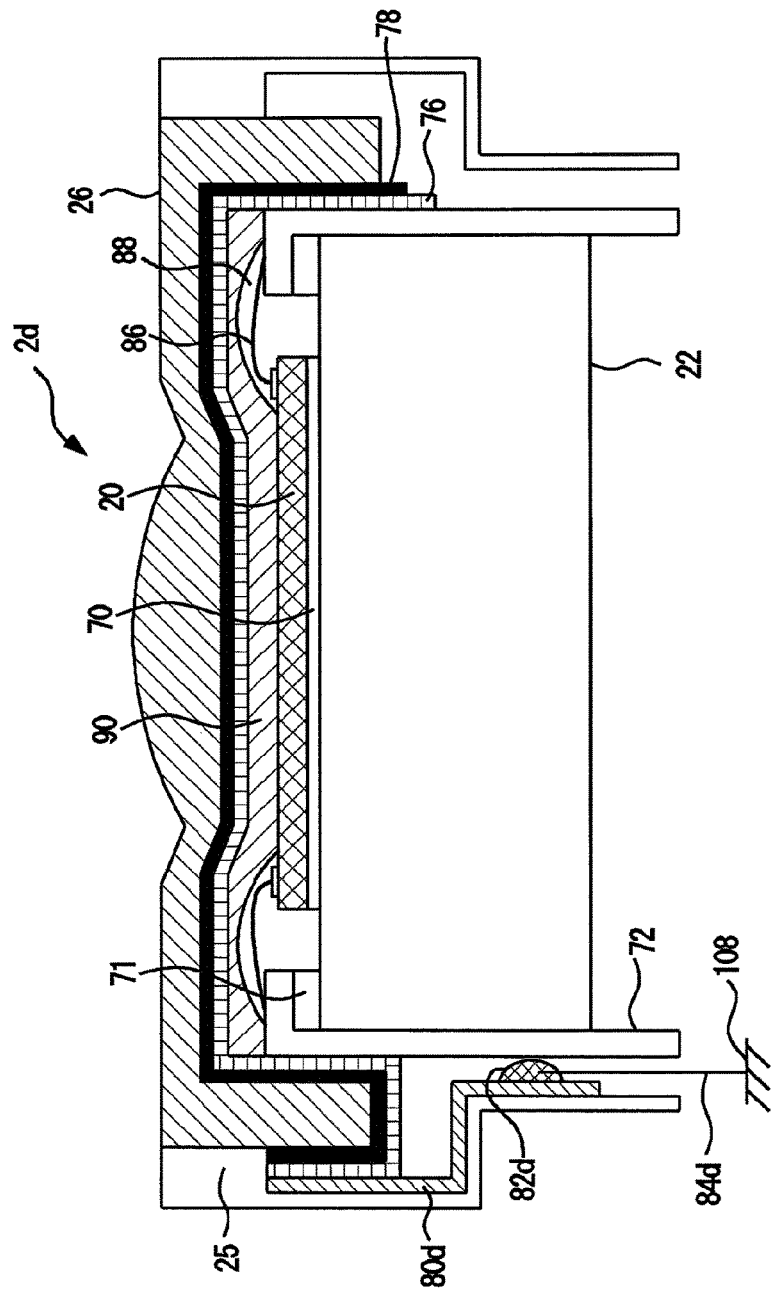
Figure 12:
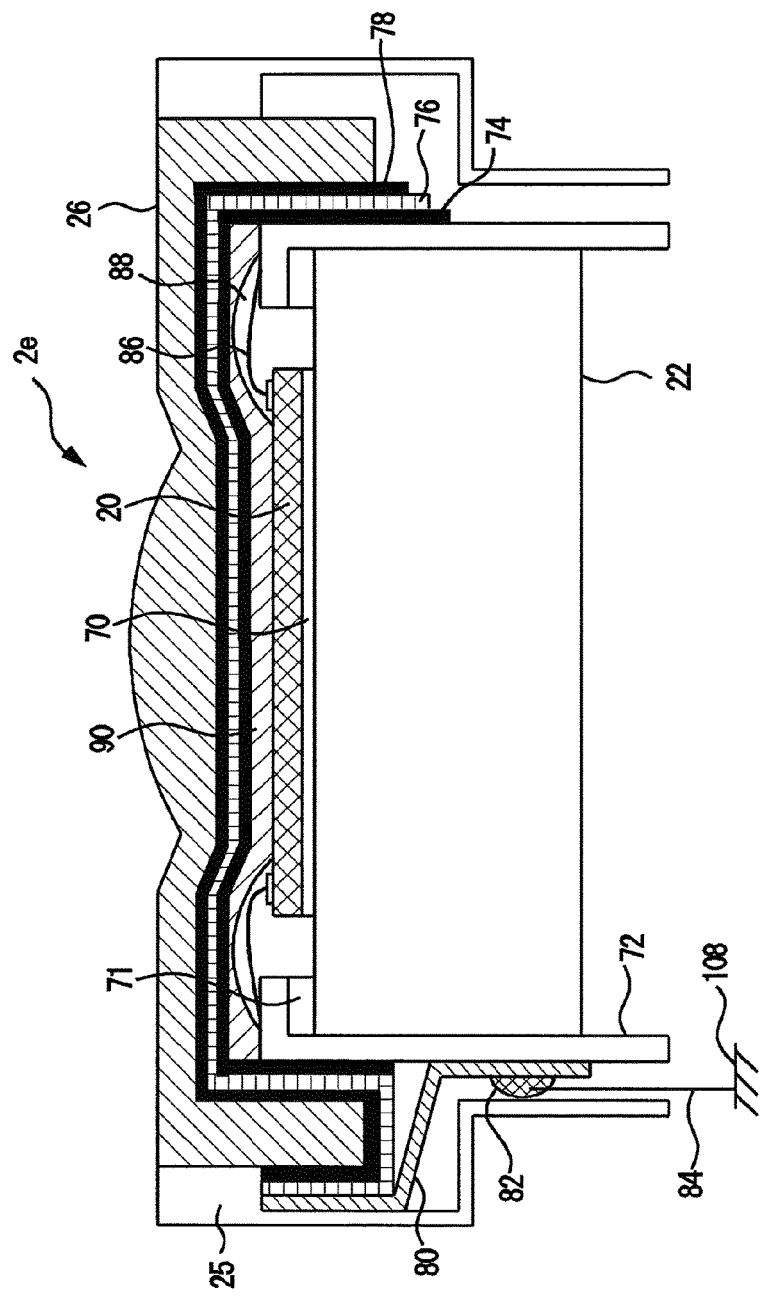
Figure 13:
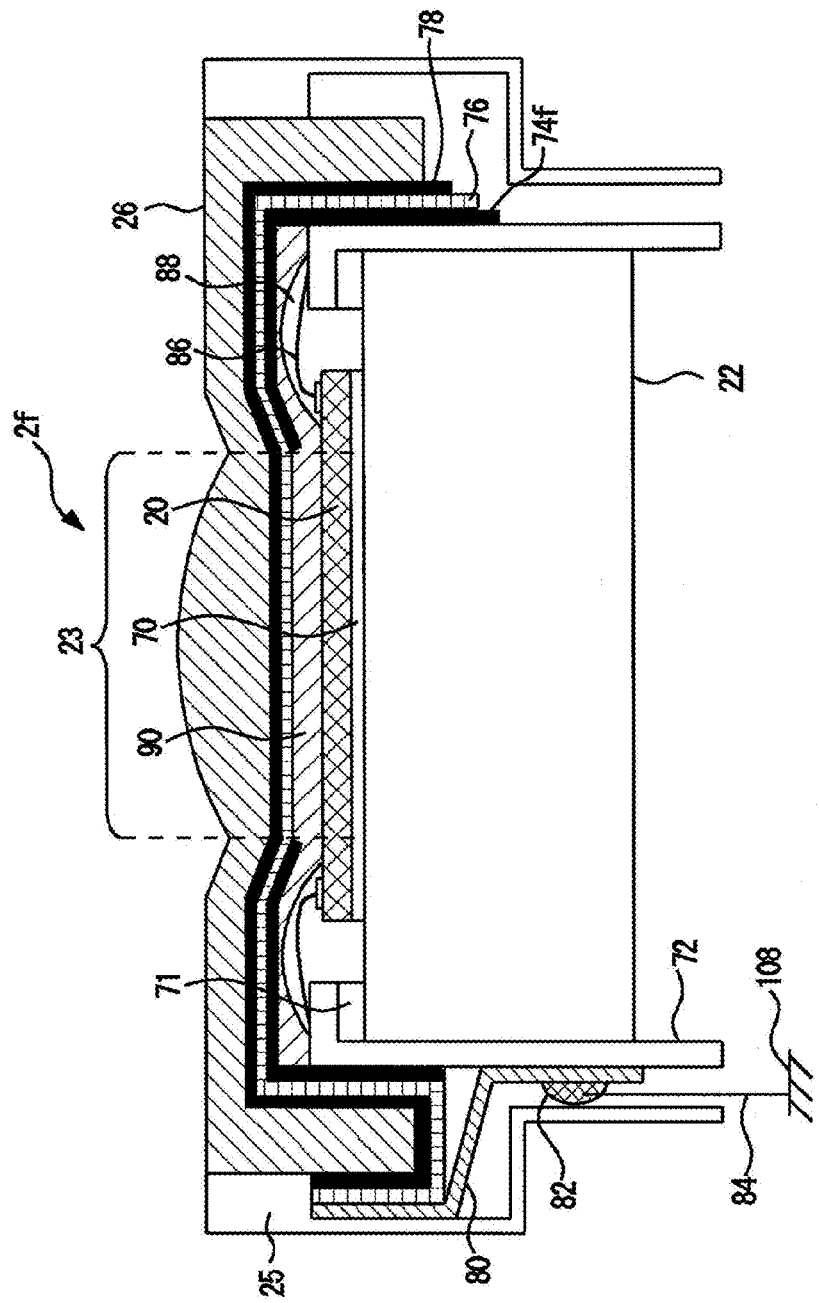
Figure 14:
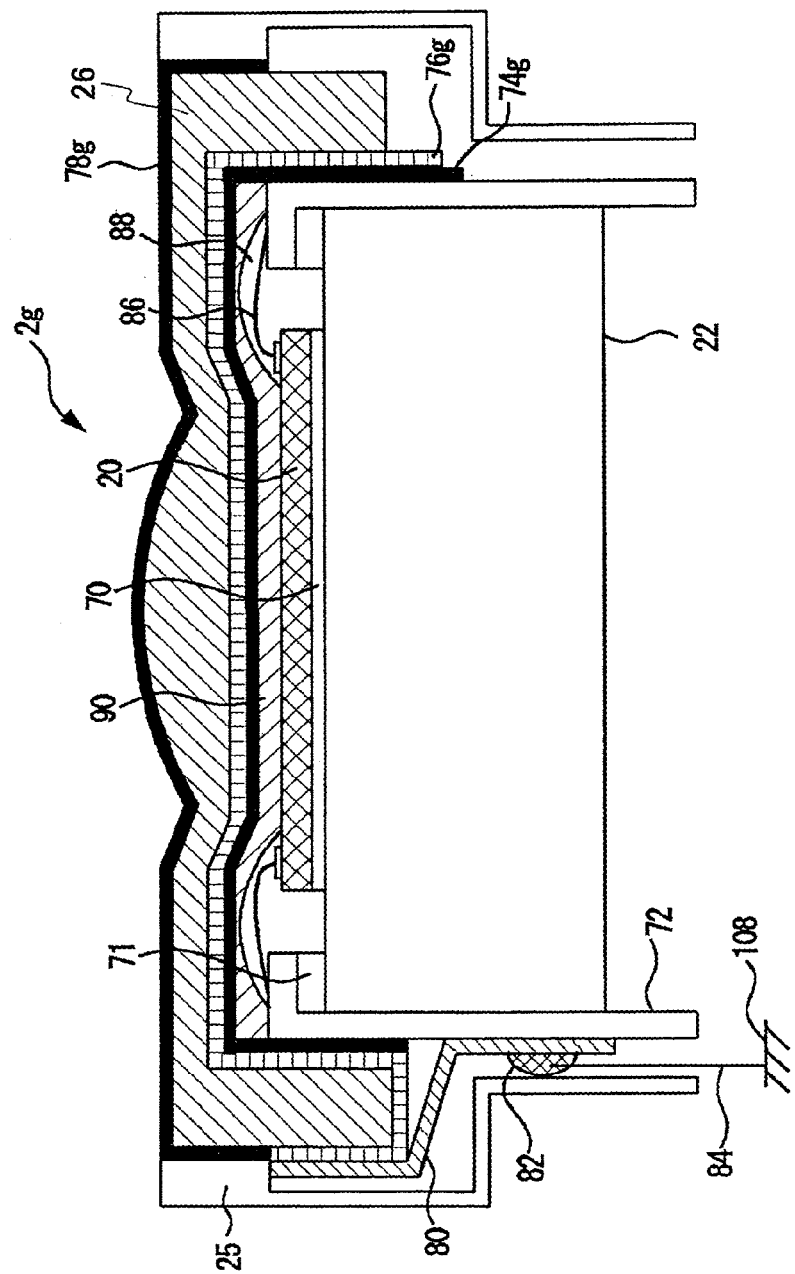
Figure 15:
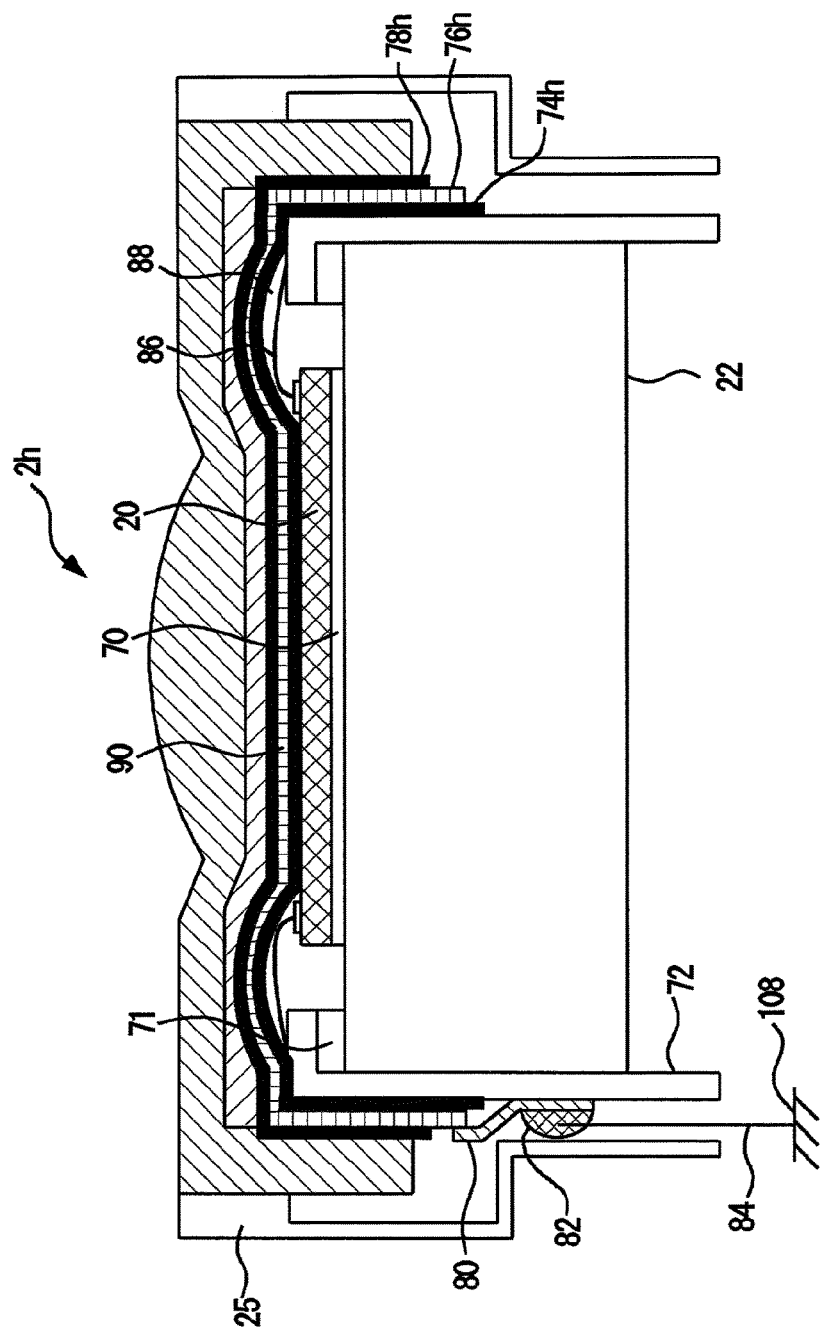

FIG. 1 is a configuration diagram showing an ultrasonic diagnostic apparatus related to the present invention.
FIG. 2 is a configuration diagram showing an ultrasonic probe related to the present invention.
FIG. 3 is a configuration diagram showing a transducer related to the present invention.
FIG. 4 is a configuration diagram of one vibration element in FIG. 3 viewed from the side.
FIG. 5 shows an ultrasonic probe related to embodiment 1.
FIG. 6 shows the wiring of the ultrasonic probe.
FIG. 7 shows an ultrasonic probe related to embodiment 2.
FIG. 8 shows an ultrasonic probe related to embodiment 3.
FIG. 9 shows an ultrasonic probe related to embodiment 4.
FIG. 10 is a pattern diagram showing conductor configuration and insulation configuration.
FIG. 11 shows an ultrasonic probe related to embodiment 5.
FIG. 12 shows an ultrasonic probe related to embodiment 6.
FIG. 13 shows an ultrasonic probe related to embodiment 7.
FIG. 14 shows an ultrasonic probe related to embodiment 8.
FIG. 15 shows an ultrasonic probe related to embodiment 9.

DESCRIPTION OF THE SYMBOLS

2*c* . . . ultrasonic probe, 20 . . . cMUT chip, 22 . . . backing layer, 23 . . . region from which ultrasonic waves are emitted, 25 . . . ultrasonic probe cover, 26 . . . acoustic lens, 70 & 71 . . . adhesion layer, 72 . . . flexible substrate, 76 . . . conductive film, 78 . . . insulating film, 80 . . . conductive material, 82 . . . connecting unit, 84 . . . ground wire, 86 . . . wire, 88 . . . wire sealing resin, 90 . . . adhesion layer, 108 . . . ground

BEST MODE FOR CARRYING OUT THE INVENTION

The preferable embodiments of the ultrasonic probe and ultrasonic diagnostic apparatus using the same related to the present invention will be described below in detail referring to the attached diagrams. In the attached diagrams, the components having the same function are denoted by the same symbols, and the repeated explanation thereof will be omitted.

First, the configuration of ultrasonic diagnostic apparatus 1 will be described referring to FIG. 1.

FIG. 1 is a configuration diagram of the ultrasonic diagnostic apparatus 1.

The ultrasonic diagnostic apparatus 1 related to the present invention is configured by ultrasonic probe 2, transmitting means 3, bias means 4, receiving means 5, phasing and adding means 6, image processing means 7, display means 8, control means 9 and operation means 10.

The ultrasonic probe 2 is for transmitting/receiving ultrasonic waves to/from an object while being applied on the object. Ultrasonic waves are emitted from the ultrasonic probe 2 to the object, and the reflected echo signals produced from the object are received by the ultrasonic probe 2.

The transmitting means 3 and the bias means 4 are for applying bias voltage to the electrodes disposed in the ultrasonic probe 2 opposite each other, superimposing a drive signal and applying, and transmitting ultrasonic waves.

The receiving means 5 is for receiving the reflected echo signals to be transmitted to the ultrasonic probe 2. The receiving means 5 further performs the process such as analog/digital conversion on the received reflected echo signals.

The phasing and adding means 6 performs phasing and adding of the received reflected echo signals. The image processing means 7 constructs a diagnostic image (for example, a tomographic image or a blood flow image) based on the phased and added reflected echo signals.

The display means 8 displays the diagnostic image constructed in the image processing means 7.

The control means 9 controls the above-described respective components.

The operation means 10 gives commands such as to start diagnosis, to the control means 9. The operation means 10 is an input device such as a trackball, keyboard or mouse.

Next, the ultrasonic probe 2 will be described referring to FIG. 2~FIG. 4.

FIG. 2 is a block diagram of the ultrasonic probe 2. FIG. 2 is a partly cutaway perspective view of the ultrasonic probe 2. The upper side of the diagram is the direction to be applied on the object and that ultrasonic waves are transmitted.

The ultrasonic probe 2 comprises a cMUT chip 20. The cMUT chip 20 is a one-dimensional array type of transducer group in which a plurality of transducers 21-1, 21-2, . . . are disposed in rectangles. Into the transducers 21-1, 21-2, . . . , a plurality of vibration elements 28 are disposed. While the probe illustrated in FIG. 2 is a linear-type probe, other types of transducer group such as a 2-dimensional array type or convex type may be used.

On the back surface of the cMUT chip 20 (lower side in the diagram), a backing layer 22 is provided. On the ultrasonic waves emitting side of the cMUT chip 20, an acoustic lens 26 is provided. The cMUT chip 20 and the backing layer 22, etc. are contained in an ultrasonic probe cover 25.

In the cMUT chip 20, on the basis of the application of bias voltage by bias means 4, the drive signals from the transmitting means 3 are converted into ultrasonic waves, and the converted ultrasonic waves are transmitted to the object.

The receiving means 5 converts the ultrasonic waves produced from the object into electric signals, and receives them as the reflected echo signals.

The backing layer 22 is a layer for absorbing the transmission of the ultrasonic waves emitted from the cMUT chip 20 to the back surface side so as to constrain the extra vibration.

The acoustic lens 26 is a lens for converging the ultrasonic beams transmitted from the cMUT chip 20. Curvature of the acoustic lens 26 is defined based on the desired binocular vision.

A matching layer may be provided between the acoustic 26 and the cMUT chip 20. The matching layer is for matching the cMUT chip 20 and the acoustic impedance of the object so as to improve the transmitting efficiency of ultrasonic waves.

FIG. 3 is a configuration diagram of a transducer 21 in FIG. 2.

On the object side of the plurality of vibration elements 28 by which the transducers 21-1, 21-2, . . . are formed, upper electrodes 46-1, 46-2, . . . are disposed, divided to be pluralized in the long-axis direction X, and wire-connected for each transducer 21. In other words, the upper electrodes 46-1, 46-2, . . . are disposed in parallel in the long-axis direction X.

On the opposite side from the object side of the plurality of vibration elements by which the transducer 21 are formed, the lower electrodes (48-1~48-4) are disposed, divided to be pluralized (into four rows in FIG. 3) in the minor-axis direction Y to be wire-connected. In other words, the lower electrodes 48-1, 48-2, 48-3, . . . are disposed in parallel in the minor-axis direction Y.

FIG. 4 is a configuration diagram (cross-section view) of one vibration element 28 shown in FIG. 3, viewed from the side.

The vibration element 28 is formed by a basal plate 40, film body 44, film body 45, upper electrode 46, frame body 47 and lower electrode 48. The vibration element 28 is formed by semiconductor micro fabrication process. It is equivalent to one element of the cMUT.

The basal plate 40 is a semiconductor substrate such as silicon, and is disposed on the lower electrode side.

The film body 44 and the frame body 47 are formed by semiconducting compound such as silicon compound. The film body 44 is provided on the object side (ultrasonic waves emitting side) of the vibration elements 28, and the frame body 47 is disposed on the back surface of the film body 44 (opposite side from the object side). The upper electrode 46 is placed between the film body 44 and the frame body 47. The film body 45 is placed between the frame body 47 and the basal plate 40, and the lower electrode 48 is placed inside of the film body 45. An internal space 50 which is comparted by the frame body 47 and the film body 45 is left as a vacuum or filled with predetermined gas.

The upper electrode 46 and the lower electrode 48 are respectively connected to the transmitting means 3 for providing alternating-current high-frequency voltage as drive signals and bias means 4 for applying direct-current voltage as bias voltage.

When ultrasonic waves are transmitted, direct-current bias voltage (Va) is applied to the upper electrode 46 and the lower electrode 48 of the vibration elements 28, and an electric field is generated by bias voltage (Va). Tensile force is generated in the film body 44 by the generated electric field, and reaches a predetermined electromechanical coupling coefficient (Sa). When the drive signals are provided from the transmitting means 3 to the upper electrode 46, the ultrasonic waves having high intensity based on the electromechanical coupling coefficient (Sa) are emitted from the film body 44.

Also, when another direct-current bias voltage (Vb) is applied to the upper electrode 46 and the lower electrode 48 of the vibration elements 28, an electric field is generated by the bias voltage (Vb). Tensile force is generated in the film body 44 by the generated electric field and reaches a predetermined electromechanical coupling coefficient (Sb). When the drive signals are provided from the transmitting means 3 to the upper electrode 46, the intense ultrasonic waves based on the electromechanical coupling coefficient (Sb) are emitted from the film body 44.

Here, in the case that the bias voltage is "Va<Vb", the electromechanical coupling coefficient is "Sa<Sb".

On the other hand, when ultrasonic waves are received, the film body 44 is excited by the reflected echo signals produced from the object, and the capacity of the internal space 50 is changed. This variation quantity of the internal space 50 is detected via the upper electrode 46 as electric signals.

The electromechanical coupling coefficient of the vibration elements 28 is determined by the tension applied on the film body 44. Therefore, if the level of bias voltage to be applied to the vibration elements 28 is changed and the tension of the film body 44 is controlled, even in the case that the drive signals having the same amplitude are inputted, the intensity (or acoustic pressure, amplitude) of the ultrasonic waves to be emitted from the vibration elements 28 can be changed.

Embodiment 1

Next, embodiment 1 of the present invention will be described referring to FIG. 5 and FIG. 6.

FIG. 5 shows the ultrasonic probe 2 related to embodiment 1. FIG. 5 is a cross-sectional view of the flat plane "A" of the ultrasonic probe 2 shown in FIG. 2.

In accordance with FIG. 5, an insulating film 78 which is an insulation layer is formed on the back surface of the acoustic lens 26. The insulating film 78 is, for example, a silicon oxide film or a paraxylene film.

The cMUT chip 20 is glued to the upper surface of the backing layer 22 via the adhesion layer 70. A flexible substrate 72 (Flexible printed circuits: FPC) is provided from the peripheral border of the upper surface of the backing layer 22 over to the side surfaces in four directions. The flexible substrate 72 is glued onto the peripheral border of the upper surface of the backing layer 22 via the adhesion layer 71.

The adhesion layer 70 and the adhesion layer 71 are an adhesive agent formed by, for example, epoxide resin. The height, direction and position of the cMUT chip 20 and the flexible substrate 72 can be adjusted by arbitrarily adjusting the layer thickness of the adhesion layer 70 and the adhesion layer 71.

The flexible substrate 72 and the cMUT chip 20 are electrically connected via a wire 86. The wire 86 is connected by the wire bonding method. As for the wire 86, Au wire, etc. can be used. A wire-sealing resin 88 is filled around the wire 86.

The acoustic lens 26 is glued onto the upper surface of the cMUT chip 20 via an adhesion layer 90. As for the material of the acoustic lens 26, for example, silicon rubber is used. In regard to the material of the adhesion layer 90, it is desirable to use a material similar to that used in the acoustic lens 26 (for example, silicon).

The upper surface of the acoustic lens 26 has a convex shape in the ultrasonic waves emitting direction in the range of at least region 23 within the region from which the ultrasonic waves are emitted. In the cMUT chip 20, the vibration elements 28 are disposed within the region corresponding at least to the region 23. Ultrasonic waves are to be irradiated from the convex portion which is on the ultrasonic waves irradiating side (toward the object side) of the acoustic lens 26.

The back surface of the acoustic lens 26 (the opposite side from the object side, which is the backing layer side) has a concave portion so that the cMUT chip 20 can be disposed therein. In this concave portion, the cMUT chip 20 and the flexible substrate 72 are fitted by the connecting portion (wire preventing resin 88).

The ultrasonic probe cover 25 is provided on the surface in four sides of the ultrasonic probe 2, and is fixed on the surface in four sides of the acoustic lens 26. An examiner is to hold the ultrasonic probe cover 25 by his/her hand to operate the ultrasonic probe 2.

FIG. 6 shows the wiring of the ultrasonic probe 2. The basal plate 40 of the cMUT chip 20 is fixed on the upper surface of the backing layer 22. The flexible substrate 72 is fixed on the peripheral border of the upper surface of the backing layer 22.

On the flexible substrate 72, signal pattern 38-1~signal pattern 38-n are disposed in pairs vertically on the diagram, and signal pattern 41-1~signal pattern 41-4 are disposed in pairs horizontally on the diagram.

The upper electrode 46-1~upper electrode 46-n are connected to the signal pattern 38-1~signal pattern 38-n. The lower electrode 48-1~lower electrode 48-4 are connected to the signal pattern 41-1~signal pattern 41-4. The spacings between the adjacent lower electrode 48-1~lower electrode 48-4 are mutually insulated.

The upper electrode 46 and the lower electrode 48 are connected to the flexible substrate 72 via the wire 86 respectively by the wire bonding method.

As for the shape of the lower electrode 48-1~lower electrode 48-4, it is desirable that it corresponds to the shape of the vibration elements 28 (for example, a hexagon) such as a waveform. In this manner, the respective vibration elements 28 can be disposed corresponding to only one of the lower common electrode 48-1~lower common electrode 48-4.

While four electrodes are disposed in the lower electrode 48-1~lower electrode 48-4, the number does not have to be limited to four.

Also, while the signal pattern 38-1~signal pattern 38-n are disposed in pairs vertically on the diagram and the signal pattern 48-1~signal pattern 48-4 are disposed in pairs horizontally on the diagram, the pattern does not have to be limited in pairs and they may be disposed only on one side.

Also, while it is described above that the wire bonding method is used to connect the signal pattern and the upper electrode or the lower electrode, the method does not have to be limited thereto and the flip chip bonding method which connects pads to pads may be used.

As described above in detail, in the ultrasonic probe 2 of embodiment 1, the insulation layer as the electric leakage preventing means for preventing the leakage of electricity from the electrode in the cMUT chip to the object is formed as the insulating film 78 between the acoustic lens 26 and the cMUT chip. The spacing between the ultrasonic wave transmitting/receiving surface and the cMUT chip is performed with double insulation by the acoustic lens and the insulation layer. In this manner, even when friction or damage is caused in the ultrasonic wave transmitting/receiving surface, electric leakage from the ultrasonic wave transmitting/receiving surface to the object or electric shock due to the leakage can be prevented whereby improving the safety of the ultrasonic probe.

Embodiment 2

Next, embodiment 2 will be described referring to FIG. 7.

FIG. 7 shows an ultrasonic probe 2*a* related to embodiment 2. FIG. 7 is equivalent to the cross-sectional view of the flat plane "A" shown in FIG. 2.

While the insulation film 78 is illustrated as being disposed in the lower surface of the acoustic lens in embodiment 1, the insulation layer which is electric leakage preventing means for preventing the leakage of electricity from the electrode in the cMUT chip to the object is disposed in the upper surface (object side) of the acoustic lens 26 as an insulation film 78*a* in embodiment 2.

In this manner, in the ultrasonic probe 2*a* of embodiment 2, the insulation layer is formed in the upper surface of the acoustic lens. The spacing between the ultrasonic wave transmitting/receiving surface and the cMUT chip is performed with double insulation by the insulation layer (insulation film) and the acoustic lens. Therefore, even when friction or damage is caused in the ultrasonic wave transmitting/receiving surface, electric leakage from the ultrasonic wave transmitting/receiving surface to the object or electric shock due to the leakage can be prevented whereby improving the safety of the ultrasonic probe, which provides the same effect as embodiment 1.

In addition, in embodiment 2, the manufacturing process of the probe is easier compared to embodiment 1 since the insulation layer is provided on the upper surface of the acoustic lens, not on the lower surface.

Embodiment 3

Next, embodiment 3 will be described referring to FIG. 8.

FIG. 8 shows an ultrasonic probe 2*b* related to embodiment 3. FIG. 8 is equivalent to the cross-sectional view of the flat plane "A" shown in FIG. 2.

While the insulation film 78 is described as being disposed on the lower surface of the acoustic lens 26 in embodiment 1, the insulation layer which is electric leakage preventing means for preventing the leakage of electricity from the electrode in the cMUT chip to the object is disposed on the upper surface of the cMUT chip 20 as an insulation film 78*b* in embodiment 3.

In this manner, in the ultrasonic probe 2*b* of embodiment 3, the insulation layer is formed on the upper surface of the cMUT chip. In the spacing between the ultrasonic wave transmitting/receiving surface and the cMUT chip, double insulation is performed by the insulation layer and the acoustic lens. Thus the same effect can be performed as embodiment 1.

Embodiment 4

Next, embodiment 4 will be described referring to FIG. 9 and FIG. 10.

FIG. 9 shows an ultrasonic probe 2*c* related to embodiment 4. FIG. 9 is equivalent to the cross-sectional view of the flat plane "A" shown in FIG. 2.

While embodiment 1 is described without the provision of a ground layer, in embodiment 4, a conductive film 76 which is the ground layer is further provided as electric leakage preventing means for preventing the leakage of electricity from the electrode in the cMUT chip to the object is provided on the back surface (the opposite side from the object side) of the insulation film 78 as an insulation layer.

The conductive film 76 is connected to a ground 108 which is the ground potential. The conductive film 76 is, for example, a Cu film. The insulation film 78 is placed on the back surface of the acoustic lens 26, and the Cu film is deposited on the back surface of the insulating film 78 to form the conductive film 76.

The conductive film 76 is formed from the internal lower surface of the acoustic lens 26 over to the external side surfaces. The conductive film 76 is connected to a ground 108 on the main apparatus side via a conductive material 80 and a ground wire 84.

The conductive material 80 is a material which has electrical conductivity. The conductive material 80 can be manufactured using a highly reliable material which is more heavy-duty compared to the conductive film 76. The conductive material 80 is, for example, a Cu tape which has higher rigidity compared to the conductive film 76. The conductive material 80 is fixed on the external side surface of the flexible substrate 72.

The ground wire 84 is connected to the conductive material 80 via the connecting portion 82 using a method such as soldering.

FIG. 10 is a pattern diagram showing the conducting structure and insulating structure.

The upper electrode 46 is connected to a reception amplifier 100 and the transmitting means 3 via a cable 96 and a transmission/reception separating circuit 98. The lower electrode 48 is connected to the bias means 4 via a cable 102.

A resistor 110 is a resistor element for stabilizing the electric potential of bias means 4 to the ground potential. A capacitor 112 is a capacitative element for bypassing signal current.

The conductive film 76 is connected to the ground wire 84, and further connected to the ground 108 via a chassis ground of the main apparatus.

In this manner, in the ultrasonic probe 2*c* in embodiment 4, the conductive film 76 as the ground layer is provided on the lower part of the insulating film 78 as an insulation layer. By such configuration, even when the acoustic lens 26 and the insulating film 78 are damaged, the conductive film 76 can prevent electric shock because of the ground potential, whereby improving electrical safety of the ultrasonic probe with respect to an object.

Also, by the conductive film 76, the ground wire 84 and the chassis ground of the main apparatus, a closed space of electric potential is formed. In other words, since the main components of the ultrasonic probe 2*c* or the main circuits of the ultrasonic diagnostic apparatus are contained in the closed space of the ground potential, it is possible to prevent the influence of unwanted electric waves from outside or exerting a bad influence upon external apparatuses due to electromagnetic waves produced from the ultrasonic probe 2*c* itself.

Also, in the ultrasonic probe 2*c* of embodiment 4, the conductive film 76 is formed from the internal lower surface of the acoustic lens 26 over to its external surfaces, and is connected to the ground 108 via the conductive material 80 and the ground wire 84 which are highly reliable.

By such configuration, the conductive film 76 can be easily and securely connected to the ground wire via the conductive material from the conductive film formed from the internal lower surface of the acoustic lens over to its external surfaces, not from the sheet-like conductive film to be pulled out by the in mold forming, whereby it is possible to improve assuredness and workability in the implementation of the apparatus.

Also, by using highly reliable conductive material, damage of conductive material upon being fixed to the flexible substrate can be prevented.

Also, while the conductive material 80 and the ground wire 84 are illustrated only on the left side surface of the flexible substrate 72 in the diagram of FIG. 9, they may be placed on any of the four side surfaces of the flexible substrate 72.

The conductive film 76 and the ground wire 84 can be connected directly. In this case, the mounting operation needs to be conducted cautiously since the conductive film 76 is thin in its thickness.

In the present embodiment, while the ground layer is provided on the back surface of the insulating film 78 (the opposite side from the object side), an intervening layer which does not conduct electricity is disposed as a film body 44 shown in FIG. 4 in a part of the cMUT chip between the ground layer and the electrode in the cMUT chip (for example, the electrode 46 in FIG. 4). Therefore, since the electrode in the cMUT chip (for example, the electrode 46 shown in FIG. 4) and the ground layer are not in contact as disclosed in Patent Document 2, there is an advantage also that the drive voltage for transmitting/receiving ultrasonic waves can be applied to the electrode on the ultrasonic wave transmitting/receiving side (object side) in the cMUT chip.

Embodiment 5

Next, embodiment 5 will be described referring to FIG. 11. FIG. 11 shows an ultrasonic probe 2d related to embodiment 5. FIG. 11 is equivalent to the cross-sectional view of the flat plane "A" shown in FIG. 2.

While the conductive material 80 is described to be fixed on the external side surfaces of the flexible substrate 72 in embodiment 4, it can be fixed on any place formed by a material capable of fixing the conductive material 80. In embodiment 5, a conductive material 80d is fixed on the internal side surfaces of the ultrasonic probe cover 25.

The conductive film 76 is connected to the ground 108 on the main apparatus side via a conductive material 80d and a ground wire 84d.

The conductive material 80d is fixed on the internal side surfaces of the ultrasonic probe cover 25. The ground wire 84d is connected to the conductive material 80d via a connecting portion 82d by a method such as soldering.

In this manner, in embodiment 5, it is possible to connect the conductive film and the ground wire easily and unfailingly as in embodiment 4 while securing high reliability.

While the conductive material 80d and the ground wire 84d are shown only on the left side of the internal side surfaces in the ultrasonic probe cover 25 of in FIG. 11, they can be placed on the internal side surface of any four sides in the ultrasonic probe cover 25.

Embodiment 6

Next, embodiment 6 will be described referring to FIG. 12. FIG. 12 shows an ultrasonic probe 2e related to embodiment 6. FIG. 12 is equivalent to the cross-sectional view of the flat plane "A" shown in FIG. 2.

While it is described that one layer of insulation is provided in embodiment 1~embodiment 5, two layers of insulation is provided in embodiment 6 having the ground layer therebetween.

Between the acoustic lens 26 and the adhesion layer 90 on the cMUT chip 20, the insulating film 78 as an upper insulation layer, the conductive film 76 as a ground layer and the insulating film 74 as a lower insulating layer are formed. The conductive film 76 is formed between the insulating film 78 and the insulating film 74.

In other words, from the direction that the ultrasonic probe 2 is applied to an object, the acoustic 26, insulating film 78, conductive film 76 and insulating film 74 are layered in order.

For details, the insulating film 78 is formed on the lower surface of the acoustic lens 26, the conductive film 76 is formed by depositing the Cu film on the lower surface of the insulating film 78, and the insulating film 74 is formed on the lower surface of the conductive film 76.

In this manner, in embodiment 6, between the ultrasonic wave transmitting/receiving surface and the cMUT chip, two layers of insulation layers are comprised having a conductive film therebetween as electric leakage preventing means for preventing the leakage of electricity from the electrode in the cMUT chip to the object. By such configuration, it is possible to improve safety by increasing insulation of the ultrasonic probe.

Also, while the ground layer is provided between the two layers of insulating films 74 and 78 in the present embodiment, the insulating film 74 is further disposed between the ground layer and the electrode in the cMUT chip as an intervening layer which does not conduct electricity (for example, the electrode 46 in FIG. 4). Therefore, since the electrode in the cMUT chip (for example, the electrode 46 in FIG. 4) and the ground layer are not in contact as disclosed in Patent Document 2, there is an advantage that the drive voltage for transmitting/receiving ultrasonic waves can be applied also to the electrode on the ultrasonic wave transmitting/receiving surface side (object side) in the cMUT chip.

Embodiment 7

Next, embodiment 7 will be described referring to FIG. 13. FIG. 13 shows an ultrasonic probe 2f related to embodiment 7. FIG. 13 is equivalent to the cross-sectional view of the flat plane "A" shown in FIG. 2.

While the insulating film 74 is described as being provided in the region indicated as region 23 in embodiment 6, an insulating film 74f in embodiment 7 is not provided in the region 23.

In this manner, in embodiment 7, the insulating film 74f is not placed on the cMUT chip 20, thus there is no influence of the insulating film 74f on the ultrasonic waves transmitted/received in the cMUT chip 20, whereby improving the acoustic characteristics.

In the above-described embodiment, it is desirable to make the film thickness of the conductive layer in the range of 0.1 µm, and the film thickness of the insulation layer in the range of 1 µm. By making the respective film thickness of the insulation layer and the conductive layer, the influence to the ultrasonic waves transmitted/received in the cMUT chip (influence or attenuation to pulse and frequency characteristic) can be restrained.

As for the method to form the films, the method to perform the in mold forming on the insulating sheet attached with the conductive film at the same time as forming the acoustic lens, or the method for forming the insulating film and the conductive film by chemical deposition can be used. While the film can be formed at low cost in the in-mold forming method, the limit of the film thickness is in the range of 10 µm. On the other hand, the film thickness can be in the range of 1 µm in the film forming by deposition method.

While the region where the insulating film is not provided within the region 23 is "74f" in the present embodiment, it may be "78" or both.

The ultrasonic probe and ultrasonic diagnostic apparatus may be configured by properly combining the above-described embodiments.

Embodiment 8

FIG. 14 shows an ultrasonic probe 2g related to embodiment 8.

In the ultrasonic probe 2g, a ground layer 76g is placed on the lower surface of the acoustic lens 26, an insulation layer 78g is further placed on the upper surface (the object side) of the acoustic lens 26, and an insulating film 74g is placed on the back surface of the ground layer 76g.

Embodiment 9

FIG. 15 shows an ultrasonic probe 2h related to embodiment 9.

The ultrasonic probe 2h is the case that the two layers of insulation layers having a conductive film therebetween is comprises as electric leakage preventing means for preventing the leakage of electricity from the electrode in the cMUT chip to an object, and an example that the conductive material 80 for connecting a conductive film 76h and the ground wire 84 is fixed on the flexible substrate 72.

While preferable embodiments of the ultrasonic probe and ultrasonic diagnostic apparatus related to the present invention have been described above referring to the attached diagrams, the description herein of specific embodiments is not intended to limit the invention to the particular forms described. On the contrary, it is apparent to those skilled in the art that the intension is to cover all modifications, equivalents and alternations falling within the spirit and scope of invention as defined by the appended claims.

The invention claimed is:

1. An ultrasonic probe comprising:
   a capacitive micro-machined ultrasonic transducer (cMUT) chip for transmitting/receiving ultrasonic waves, and including a plurality of vibration elements having an electromechanical coupling coefficient or sensitivity which varies in accordance with bias voltage;
   an acoustic lens disposed on the ultrasonic wave emitting side of the cMUT chip;
   an insulating layer disposed between the acoustic lens and an upper electrode of the cMUT chip to which a drive signal applied; and
   a ground layer disposed between the acoustic lens and the insulation layer.

2. The ultrasonic probe according to claim 1, wherein the insulation layer is a part of the cMUT chip, and is disposed on the bias voltage applied electrode.

3. The ultrasonic probe according to claim 2, wherein the insulation layer is a film body.

4. The ultrasonic probe according to claim 1, wherein the insulation layer comprises two layers of insulation material and a ground layer disposed between the two layers of insulation material.

5. The ultrasonic probe according to claim 1, wherein the insulation layer is a paraxylene film.

6. The ultrasonic probe according to claim 1, wherein the ground layer is a Cu film.

* * * * *